United States Patent [19]
Wulfman et al.

[11] Patent Number: 6,156,048
[45] Date of Patent: *Dec. 5, 2000

[54] ATHERECTOMY DEVICE FOR REDUCING DAMAGE TO VESSELS AND/OR IN-VIVO STENTS

[75] Inventors: Edward Wulfman, Woodinville; Lucas Gordon, Redmond; Robert Barry, Kirkland; Brandon Shuman, Seattle; David Dillard, Redmond; Verivada Chandrasekaran, Mercer Island, all of Wash.

[73] Assignee: SCIMED Life Systems, Inc., Maple Grove, Minn.

[*] Notice: This patent is subject to a terminal disclaimer.

[21] Appl. No.: 09/365,188

[22] Filed: Aug. 2, 1999

Related U.S. Application Data

[63] Continuation of application No. 09/035,734, Mar. 5, 1998, Pat. No. 6,015,420, which is a continuation-in-part of application No. 08/813,827, Mar. 6, 1997, abandoned, which is a continuation-in-part of application No. 08/812,715, Mar. 6, 1997, abandoned.

[51] Int. Cl.[7] .................................................. A61B 17/22
[52] U.S. Cl. ............................................................. 606/159
[58] Field of Search .................................... 606/159, 180, 606/170, 171, 168; 604/22

[56] References Cited

U.S. PATENT DOCUMENTS

| | | |
|---|---|---|
| 1,112,982 | 10/1914 | Conine . |
| 1,612,697 | 12/1926 | Cecil . |
| 3,352,303 | 11/1967 | Delaney . |
| 3,894,673 | 7/1975 | Lowder et al. . |
| 4,018,576 | 4/1977 | Lowder et al. . |
| 4,445,509 | 5/1984 | Auth . |
| 4,572,186 | 2/1986 | Gould . |
| 4,646,736 | 3/1987 | Auth . |
| 4,650,466 | 3/1987 | Luther . |
| 4,679,557 | 7/1987 | Opie et al. . |
| 4,732,154 | 3/1988 | Shiber . |
| 4,771,774 | 9/1988 | Simpson et al. . |
| 4,885,003 | 12/1989 | Hillstead . |
| 4,895,560 | 1/1990 | Papantonakos . |
| 4,921,484 | 5/1990 | Hillstead ................. 606/159 |
| 4,950,238 | 8/1990 | Sullivan . |
| 4,976,690 | 12/1990 | Solar et al. . |
| 4,990,134 | 2/1991 | Auth . |
| 5,030,201 | 7/1991 | Palestrant . |
| 5,034,001 | 7/1991 | Garrison et al. . |
| 5,100,425 | 3/1992 | Fischell et al. . |
| 5,116,350 | 5/1992 | Stevens . |
| 5,135,483 | 8/1992 | Wagner et al. . |

(List continued on next page.)

FOREIGN PATENT DOCUMENTS

| | | |
|---|---|---|
| 0 086 048 | 8/1983 | European Pat. Off. . |
| 0 117 519 A1 | 2/1984 | European Pat. Off. . |
| 0 267 539 | 5/1998 | European Pat. Off. . |
| 43 34 266 A1 | 4/1994 | Germany . |
| 2 020 557 | 5/1979 | United Kingdom . |
| WO 92/03097 | 3/1992 | WIPO . |
| WO 92/03098 | 3/1992 | WIPO . |
| WO 93/01753 | 2/1993 | WIPO . |
| WO 93/01849 | 2/1993 | WIPO . |
| WO 93/19679 | 10/1993 | WIPO . |
| WO 94/08519 | 4/1994 | WIPO . |

*Primary Examiner*—Michael Buiz
*Assistant Examiner*—Kevin Truong
*Attorney, Agent, or Firm*—Christensen O'Connor Johnson & Kindness PLLC

[57] ABSTRACT

An atherectomy device that may reduce the risk of damage to a vessel wall. One rotatable atherectomy burr has a recessed material removal portion lying between less abrasive proximal and distal shoulders. The shoulders can have a straight, rounded or elliptical taper. The shoulders can perform a cam action when the burr is canted is a vessel, as when passing the burr and guide wire through a tortuous, stenosed vessel path. The shoulders act to align the burr with the path through the vessel, presenting the less abrasive shoulders to the vessel wall while presenting the abrasive portion to a stenosis.

3 Claims, 4 Drawing Sheets

U.S. PATENT DOCUMENTS

| | | |
|---|---|---|
| 5,135,531 | 8/1992 | Shiber . |
| 5,154,724 | 10/1992 | Andrews . |
| 5,176,693 | 1/1993 | Pannek, Jr. . |
| 5,217,474 | 6/1993 | Zacca et al. . |
| 5,224,945 | 7/1993 | Pannek, Jr. . |
| 5,250,060 | 10/1993 | Carbo et al. . |
| 5,314,407 | 5/1994 | Auth et al. . |
| 5,314,438 | 5/1994 | Shturman ................................ 606/170 |
| 5,395,311 | 3/1995 | Andrews . |
| 5,490,859 | 2/1996 | Mische et al. . |
| 5,501,694 | 3/1996 | Ressemann et al. . |
| 5,569,276 | 10/1996 | Jang et al. . |
| 5,634,928 | 6/1997 | Fischell et al. . |
| 5,649,941 | 7/1997 | Lary . |
| 5,667,490 | 9/1997 | Keith et al. . |
| 5,749,883 | 5/1998 | Halpern ................................... 606/159 |
| 5,843,090 | 12/1998 | Shuetz . |

ATHERECTOMY DEVICE FOR REDUCING DAMAGE TO VESSELS AND/OR IN-VIVO STENTS

CROSS REFERENCE TO CO-PENDING APPLICATIONS

This application is a continuation of prior application Ser. No. 09/035,734, filed Mar. 5, 1998 now U.S. Pat. No. 6,015,420 which is a continuation-in-part of U.S. patent application Ser. No. 08/813,827 now abandoned and U.S. patent application Ser. No. 08/812,715 now abandoned, both filed on Mar. 6, 1997, both entitled "Atherectomy Device For Reducing Damage To Vessels and/or In-Vivo Stent" and both assigned to the assignee of the present invention.

TECHNICAL FIELD

The present invention generally relates to atherectomy devices. More specifically, the present invention relates to atherectomy burrs having shoulders which can align the burr with a stenosed path through blood vessels.

BACKGROUND OF THE INVENTION

Vascular diseases, such as atherosclerosis and the like, have become quite prevalent in the modern day. These diseases may manifest themselves in a number of ways, often requiring different forms or methods of treatment for curing the adverse effects of the diseases. Vascular diseases, for example, may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. While a number of effective invasive therapies are available, it is desired to develop non-invasive therapies as well. Non-invasive therapies may be more desirable because of the possibility of decreased chances of infection, reduced post-operative pain, and less post-operative rehabilitation. Drug therapy is one type of non-invasive therapy developed for treating vascular diseases. Clot-busting drugs have been employed to help break up blood clots which may be blocking a particular vascular lumen. Other drug therapies are also available. Further non-invasive intravascular treatments exist that are not only pharmaceutical, but also physically revascularize lumens. Two examples of such intravascular therapies are balloon angioplasty and atherectomy, both of which physically revascularize a portion of a patient's vasculature.

Balloon angioplasty is a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and is then inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It should be recognized that this procedure does not remove the matter from the patient's vasculature, but displaces and reforms it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus may not be prone or susceptible to angioplastic treatment. Even if angioplasty is successful, there is a chance that the occlusion may recur. Recurrence of an occlusion may require repeated or alternative treatments given at the same intravascular site.

A relatively new technique to reduce the recurrence of occlusion after a balloon angioplasty procedure involves providing a stent at the revascularized site. A stent is typically a hollow tube, typically braided, that can be inserted into the vascular of a patient in a compressed form. Once properly positioned at a desired site, the stent is expanded to hold the vessel open in an attempt to prevent restenosis. While this technique can help maintain blood flow past the site, it has been found that the occluding material often migrates through the interstices of the stent braid, and may again occlude the vessel. This phenomenon is sometimes referred to as interstitial hyperplasia.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty, drug and/or stent therapies.

One such alternative mechanical treatment method involves removal, not displacement of the material occluding a vascular lumen. Such treatment devices, sometimes referred to as atherectomy devices, use a variety of material removal means, such as rotating cutters or ablaters for example, to remove the occluding material. The material removal device is typically rotated via a drive shaft that extends out of the vascular of the patient and to an electric motor.

In operation, an atherectomy device is typically advanced over a guide wire placed in-vivo until the material removal device is positioned just proximal to the occluded site. The motor is used to rotate the drive shaft and the material removal device, and the material removal device is moved through the occluded vessel. The material removal device removes the material from the vessel, rather than merely displacing or reforming the material as in a balloon angioplasty procedure.

A danger for all atherectomy devices is the unwanted perforation of a vessel wall by the material removal device. This can occur when the material removal device improperly engages the vessel wall, for example when the material removal device is not oriented substantially parallel to the axis of the vessel. In this situation, the material removal device (e.g. cutter or abrasive ablater) may improperly engage the vessel wall and cause unwanted damage thereto.

Similarly, an atherectomy device may cause damage to an in-vivo stent when used to remove occluding material from within the stent caused by, for example, interstitial hyperplasia. Even a properly oriented material removal device may damage a stent. If the cutter or ablater of a typical atherectomy device engages a stent, particulates of the stent and/or material removal device may be removed and introduced into the vasculature of the patient. As is known, this is undesirable and can be dangerous to the patient. To reduce this risk, the material removal device typically has an outer diameter that is substantially less than the inner diameter of the stent. It is believed that this may reduce the risk that the material removal device will engage and thus damage, the stent. A limitation of this approach is that a substantial gap typically must be provided between the material removal device and the stent. This may reduce the amount of occluding material that can be removed from within the stent. Accordingly, the stent will likely become occluded sooner than if the outer diameter of the material removal device could more closely match the inner diameter of the stent, and remove more of the occluding material.

Given the above-discussed considerations, it would be desirable to provide an atherectomy device that can reduce the risk of damage to a vessel wall and/or an in-vivo stent. In particular, it would be advantageous to provide an atherectomy device that can align the burr cutting action with a path through the stenosed vessel while removing unwanted material and yet not cause excessive wear on the vessel walls.

SUMMARY OF THE INVENTION

The present invention overcomes many of the disadvantages of the prior art by providing an atherectomy device that may reduce the risk of damage to a vessel wall and/or an in-vivo stent. In one embodiment of the present invention, an atherectomy device is provided that has a rotatable ablation burr attached to the distal end of a flexible drive shaft. The ablation burr can have generally elliptical proximal and distal shoulders and a generally cylindrical material removal portion therebetween. In a preferred embodiment, the material removal portion is substantially cylindrical and is recessed relative to the shoulders. In a preferred embodiment, the material removal portion contains abrasive material such as diamond grit adhered to the outer surface.

The proximal and distal shoulders are substantially less abrasive than the material removal portion. The shoulders are tapered and act to align the burr along a path through the stenosed vessel. Aligning the burr allows an unwanted, projecting deposit to be presented to the material removal portion while the less abrasive shoulders are presented to the vessel wall. The shoulders can serve to re-align the burr when the burr assumes a cant due to a tortuous path through a stenosed vessel.

In another embodiment of the present invention, an atherectomy device is provided that has a flexible drive shaft with an ablation burr attached to the distal end thereof. The ablation burr is preferably generally elliptical in shape except for a concave shaped leading surface. An abrasive grit is then disposed on the concave shaped leading surface. Extending distally from the concave shaped leading surface is a distal tip portion, and extending proximally from the concave shaped leading surface is a convex shaped portion. Both the distal tip portion and the convex shaped portion have non-abrasive surfaces.

In this configuration, the abrasive grit is effectively prevented from engaging a vessel wall regardless of the orientation of the ablation burr within the vessel. That is, the non-abrasive surfaces of the distal tip and the convex shaped portion will tend to engage the vessel wall before the concave shaped leading surface, and may effectively prevent the abrasive grit of the concave shaped leading surface from engaging the vessel wall. To further reduce the friction between the ablation burr and the vessel wall, the convex shaped portion may have a number of dimples formed therein.

It is recognized that the benefits of this embodiment may equally apply when the ablation burr is used to remove unwanted deposits from within a stent (e.g. interstitial hyperplasia). In this application, however, the present invention may effectively prevent the abrasive grit on the concave shaped leading surface from engaging the stent, rather than the interstitial hyperplasia. This may reduce the risk of damage to the stent.

In another embodiment of the present invention, the ablation burr may include an outer surface which is generally non-abrasive, but has a number of depressions therein forming a number of depressed surfaces. An abrasive is provided only on the depressed surfaces. In this configuration, all of the abrasive is positioned just below the outer surface of the ablation burr. Accordingly, only the non-abrasive outer surface of the ablation burr contact the stent. The occluding material within the stent, however, may enter the depressions and become ablated. Preferably, the depressions form a number of depressed flutes in the outer surface of the ablation burr.

In another embodiment of the present invention, the ablation burr has a generally elliptical outer surface with a selected portion of the outer surface having an abrasive coating. The abrasive coating is formed from a material that is softer than the material used to form the stent. Accordingly, the abrasive may not damage the stent. In a preferred embodiment, the abrasive includes a number of chips or a grit that comprises plastic or some other malleable material that is softer than the material used to form the stent. It is known that stents are typically formed from stainless steel or Nitinol.

Finally, and in another embodiment of the present invention, the atherectomy device includes a cutter device rather than an ablation device on distal end thereof. The cutter device may be generally elliptical in shape, and may have a number of cutter blades on at least a leading surface thereof. In this embodiment, at least a portion of selected cutter blades are made from a material that is softer than the material used to form the stent. As indicated above, stents are typically made from either stainless steel or Nitinol. In the present embodiment, it is contemplated that the cutter blades can be made from a softer material such as aluminum, titanium or annealed stainless steel. These materials are advantageous in that they are very ductile. It is contemplated, however, that the cutting blades may be surface hardened by oxidizing, nitriding, cabonizing or by some other process to maintain a sharp cutting edge. A sharp cutting edge is often important to minimize the particle size of the ablated atheroma. If the burr contacts the stent, the underlying ductile burr material preferably plastically deforms, thus preventing particle generation from either the burr or the stent.

An advantage of all of these embodiments is that the material removal device (e.g. cutter or ablater) can have an outer diameter that more closely matches the inner diameter of a stent. In prior atherectomy devices, the material removal device typically had an outer diameter that was substantially less than the inner diameter of the stent to reduce the risk that the material removal device will engage, and thus damage, the stent. However, in the present invention, appropriate portions of the material removal devices are formed from a softer material than the stent. This may allow the material removal device to engage the stent without substantially damaging the stent. Accordingly, the present invention may allow the material removal device to have an outer diameter that more closely matches the inner diameter of the stent, which may allow the material removal to remove more of the occluding matter from the stent.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
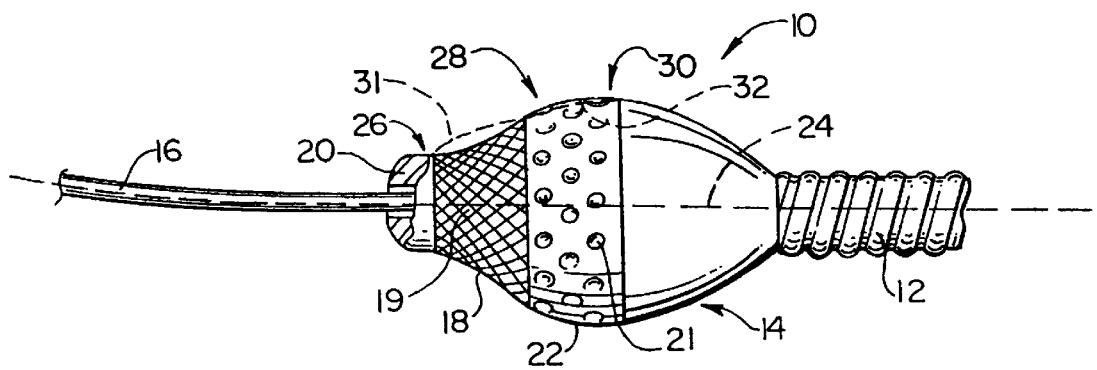
FIG. 1 is a side elevational view of an atherectomy device in accordance with a first embodiment of the present invention, including a concave shaped leading surface.

FIG. 1 is a side elevational view of an atherectomy device in accordance with a first embodiment of the present invention. The atherectomy device is generally shown at 10, and includes a flexible drive shaft 12 and an ablation burr 14. The flexible drive shaft 12 and ablation burr 14 have a lumen extending therethrough to receive a guide wire 16, as shown. In operation, the guide wire 16 is percutaneously inserted through the vascular, and past the desired occlusion site. The atherectomy device 10 is then slid over the guide wire 16 until the ablation burr 14 is positioned just proximal to the occlusion site. A guide catheter may be used to assist in the positioning of both the guide wire 16 and the atherectomy device 10, as is known in the art. The proximal end of the drive shaft remains outside the body and is attached to an electric motor. The motor rotates the atherectomy device while the atherectomy device is advanced distally through the occlusion site. The ablation burr 14 removes the occluding material by ablation.

Preferably, the atherectomy device 10 comprising a flexible drive shaft 12 attached to an ablation burr 14, wherein the flexible drive shaft 12 and the ablation burr 14 are disposed about a central axis 24. The ablation burr 14 has a first cross section 26 spaced from a second cross section 28, wherein the second cross section 28 has a larger cross sectional area than the first cross section 26. The ablation burr 14 further has a first outer surface 18 that extends between the first cross section 26 and the second cross section 28, and extends inward toward the central axis 24 relative to an imaginary line 31 that extends between the first cross section 26 and the second cross section 28 as shown.

The atherectomy device 10 may further have a third cross section 30 spaced relative to the second cross section 28, wherein the ablation burr 14 includes a second outer surface 22 that extends between the second cross section 28 and the third cross section 30. The second outer surface 22 extends outward away from the central axis 24 relative to an imaginary line 32 that extends between the second cross section 28 and the third cross section 30.

More specifically, and in a preferred configuration, the ablation burr 14 is generally elliptical in shape, except for a concave shaped leading surface 18 as shown. An abrasive grit 19, shown in a cross hatch, is disposed on the concave shaped leading surface 18. The abrasive grit may be a diamond grit. Extending distally from the concave shaped leading surface 18 is a distal tip portion 20, and extending proximally from the concave shaped leading surface 18 is a convex shaped portion 22. Both the distal tip portion 20 and the convex shaped portion 22 preferably have non-abrasive surfaces. In this configuration, the abrasive grit 19 is effectively prevented from engaging a vessel wall regardless of the orientation of the ablation burr 14 within a vessel. This is shown and described in more detail with reference to FIG. 2.

Figure 2:
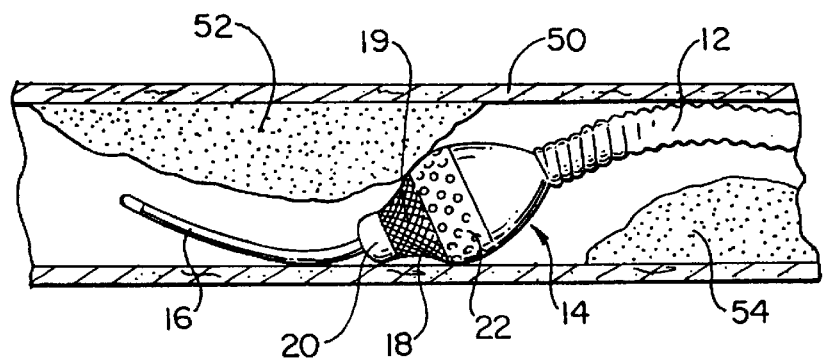
FIG. 2 is a side elevational view of the embodiment shown in FIG. 1 ablating an occluded vessel.

FIG. 2 shows a vascular lumen 50 having occlusion material 52 and 54 disposed therein. To traverse the vascular lumen 50, the guide wire 16 may have to assume an "S" shape as shown. This configuration may cause the ablation burr 14 to be oriented at an angle relative to the central axis of the vascular lumen 50. When this occurs, the non-abrasive surfaces of the distal tip 20 and the convex shaped portion 22 will tend to engage the wall of the vessel 50 before the concave shaped leading surface 18, and may effectively prevent the abrasive grit 19 from engaging the vessel wall. Preferably, the convex shaped portion 22 has a number of dimples 21 formed therein to reduce the friction between the ablation burr 14 and the wall of the vessel 50.

It is recognized that the ablation burr 14 may become offset from the central axis of a lumen for a number of reasons, and the above example is only illustrative. Another illustrative example is when the atherectomy device 10 is substantially less flexible than the guide wire 16, which is usually the case. In this situation, and when a relatively sharp bend in the vascular lumen is encountered, the atherectomy device may tend to bend the guide wire toward a vessel wall. This may cause the ablation burr 14 to improperly engage the vessel wall.

Figure 3:
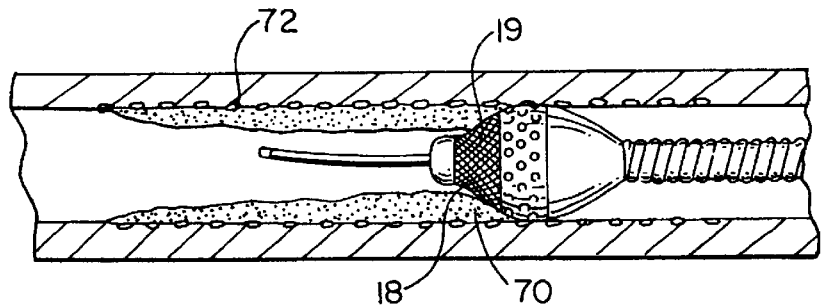
FIG. 3 is a side elevational view of the embodiment shown in FIG. 1 ablating an occluded stent.

FIG. 3 is a side elevational view of the embodiment shown in FIG. 1 ablating an occluded stent. It is recognized that the benefits of the embodiment shown in FIG. 1 may equally apply when the ablation burr is used to remove unwanted deposits (e.g. interstitial hyperplasia) 70 from within a stent 72. In this application, however, the present invention may effectively prevent the abrasive grit 19 on the concave shaped leading surface 18 from engaging the stent 72, rather than the vessel wall. This may reduce the risk that the ablating burr 14 will damage the stent 72. Accordingly, the ablating burr 14 may have an outer diameter that more closely matches the inner diameter of the stent 72.

Finally, it is contemplated that the material used to form the distal tip 20 and the convex shaped portion 22 may be softer than the material used to form the stent 72. This may further reduce the chance that the ablating burr 14 will damage the stent 72.

Figure 4:
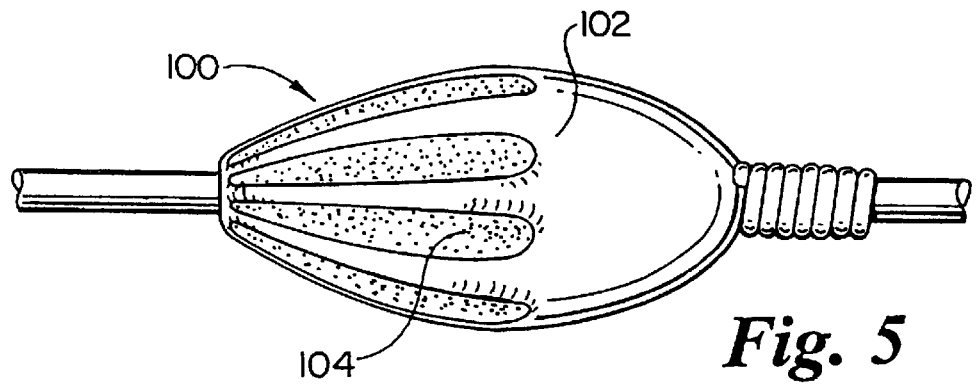
FIG. 4 is a side elevational view of an atherectomy device in accordance with another embodiment of the present invention, including a number of fluted depressions in the outer surface of the ablating burr.
Figure 5:
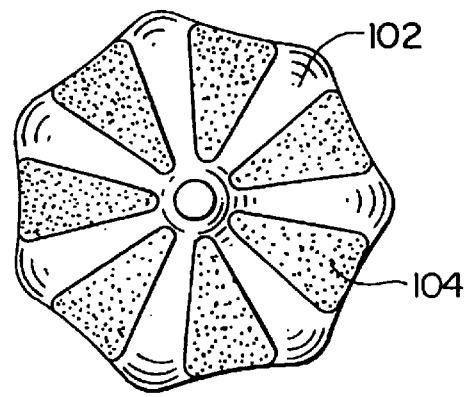
FIG. 5 is a front view of the embodiment shown in FIG. 4.

FIG. 4 is a side elevational view of an atherectomy device in accordance with another embodiment of the present invention, including a number of fluted depressions in the outer surface of the ablating burr. FIG. 5 is a front view of the embodiment shown in FIG. 4. In this embodiment, the ablation burr 100 includes an outer surface 102 which is generally non-abrasive, and a number of depressions 104 formed therein. Each of the number of depressions 104 form a depressed surface. An abrasive is provided on each of the depressed surfaces as shown, such that the abrasive is located just below the outer surface 102 of the ablation burr 100. In this configuration, only the non-abrasive outer surface 102 of the ablation burr 100 contacts the stent, and the occluding material within the stent enters the depressions 104 and becomes ablated. Preferably, the abrasive is a diamond grit, and the number of depressions 104 form a number of depressed flutes in the outer surface 102 of the ablation burr 100, as shown.

Figure 6:
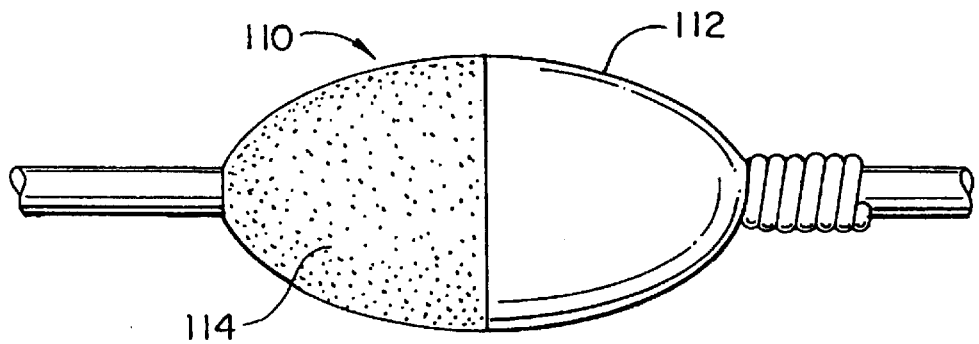
FIG. 6 is a side perspective view of another embodiment of the present invention, including an abrasive outer surface that is formed from a material that is softer than the material used to form the stent.

In another embodiment of the present invention, and as shown in FIG. 6, the ablation burr 110 has a generally elliptical outer surface 112 with a selected portion of the outer surface 114 covered with an abrasive. Preferably, the abrasive 114 is applied to either the entire outer surface 112 or to just the leading half of the outer surface 112.

In accordance with the present invention, the abrasive surface 114 is formed from a material that is softer than the material used to form the stent. Thus, the abrasive may not damage the stent if the material removal device engages the stent. Preferably, the abrasive comprises a number of chips or a grit of plastic or some malleable material which is softer than the material used to form the stent. It is known that stents are typically formed from stainless steel or Nitinol.

Figure 7:
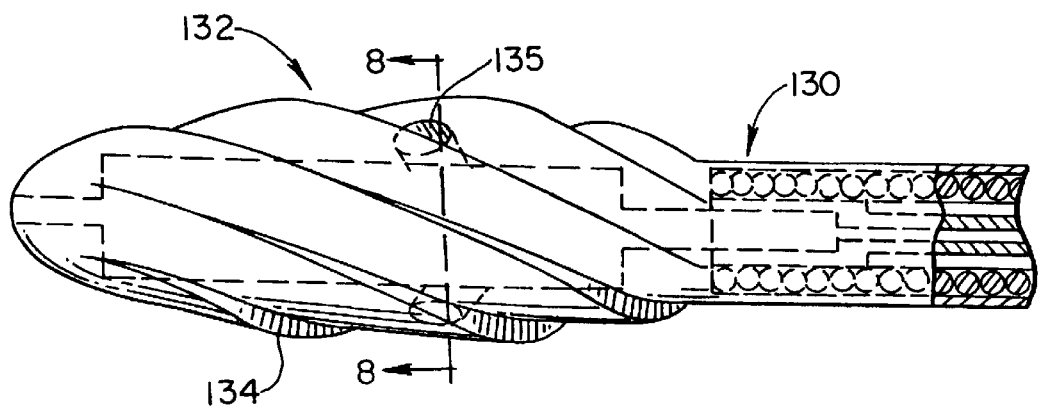
FIG. 7 is a partial cross sectional view of another embodiment of the present invention including a number of cutter blades.
Figure 8:
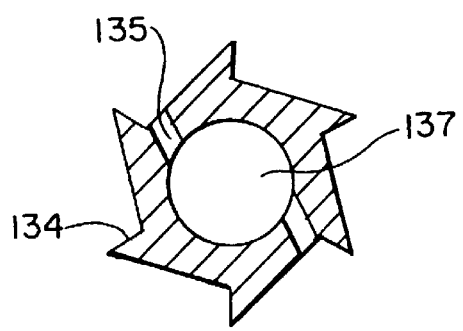
FIG. 8 is a cross-sectional side view taken along lines 8—8 of FIG. 7.

In another embodiment, and as shown in FIG. 7, the atherectomy device includes a cutter device 132 rather than an ablation device as described above. FIG. 8 is a cross-sectional side view taken along lines 8—8 of FIG. 7. The cutter device 132 may be generally elliptical in shape as shown, and may have a number of cutter blades 134 on the outer surface thereof. In accordance with the present invention, at least a portion of the cutter blades 134 are made from a material that is softer than the material used to form the stent. As indicated above, stents are typically made from either stainless steel or Nitinol. In the present embodiment, it is contemplated that selected portions of the cutter blades 134 are made from a softer material such as aluminum (e.g. an aluminum alloy 1060-0), pure titanium or annealed stainless steel. These materials are advantageous in that they are very ductile. It is contemplated, however, that the cutting blades 134 may be hardened by oxidizing, nitriding, cabonizing or by some other process to maintain a sharp cutting edge. A sharp cutting edge is often important to minimize the particle size of the ablated atheroma. If the burr contacts the stent, the underlying ductile burr material preferably plastically deforms, thus preventing particle generation from either the burr or the stent.

In the illustrative embodiment, holes 135 connect the outside of the burr (cutting surface) to the inner guide wire lumen 137. The holes 135 may be spaced at any angular interval around the diameter of the burr and at multiple points along the length of the burr. For optimum performance, the holes are preferably angled relative to an axis that is perpendicular to the central axis of the burr, as shown.

The holes 135 preferably perform one or more tasks. For example, the holes 135 may aspirate the ablated material when a vacuum is applied to the inner guide wire lumen 137. Aspiration of the ablated material may help keep the ablated particulate from being embolized distally of the ablation site. Alternatively, the holes 135 may infuse fluid to the ablation site. The infusion of fluids may help cool the site (and thus help prevent restenosis) and/or may help lubricate the ablation site to make it more difficult to unintentionally cut a vessel wall or ablate a stent.

Figure 9:
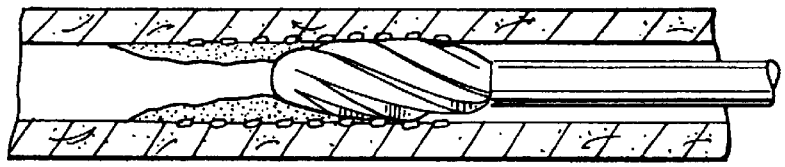
FIG. 9 is a side elevational view of the embodiment shown in FIG. 7 cutting through an occluded stent.

FIG. 9 is a side elevational view of the embodiment shown in FIG. 7 cutting through an occluded stent. Because the cutter blades 134 are made from a material that is softer than the material used to form the stent, the outer diameter of the cutter device 132 may more closely match the inner diameter of the stent. This is an advantage of all of the above embodiments. That is, in prior atherectomy devices, the material removal device typically had an outer diameter that was substantially less than the inner diameter of the stent to reduce the risk that the material removal device will engage, and thus damage, the stent. In the present invention, however, appropriate portions of the material removal devices (e.g. ablaters or cutters) may be formed from a softer material than the stent, which may protect the stent. In addition, the abrasive surfaces may be designed to not engage the stent. Accordingly, the material removal device may have an outer diameter that more closely matches the inner diameter of the stent, which may allow the material removal device to remove more of the occluding matter from within the stent.

Figure 10:
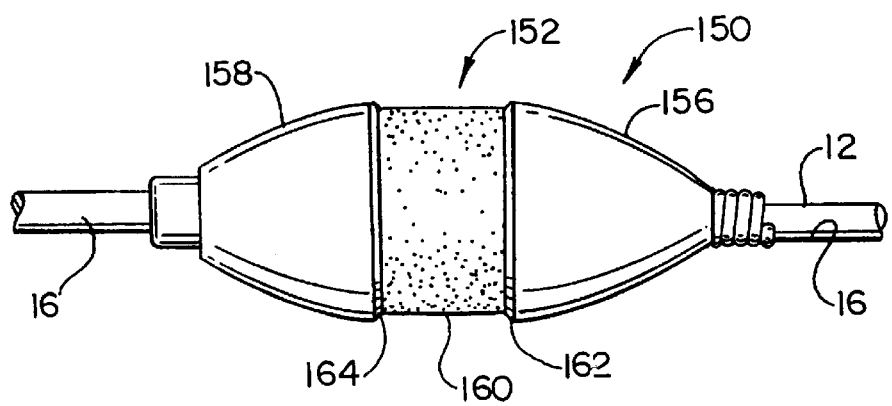
FIG. 10 is a fragmentary, side, perspective view of an atherectomy device having a guide wire disposed therethrough.

Referring now to FIG. 10, an atherectomy device 150 is illustrated, having an atherectomy burr 152 for removing unwanted material. Burr 152 includes a proximal shoulder 156, a distal shoulder 158, and is secured to the distal end of flexible drive shaft 12. Drive shaft 12 and burr 152 have a lumen therethrough, allowing passage of guide wire 16. An intermediate material removal portion 160 lies between proximal shoulder 156 and distal shoulder 158. In the preferred embodiment, illustrated in FIG. 10, material removal portion 160 is abrasive. One embodiment contains abrasive grit secured to the burr outer surface. Another embodiment includes abrasive chips fixed to the outer surface. A preferred abrasive material includes diamonds. Yet another embodiment includes cutting blades in the material removal portion.

In the embodiment illustrated, abrasive portion 160 is recessed relative to the proximal and distal shoulders, having a smaller radial extent and circumference than the maximum radial extent of either of the shoulders. In a preferred embodiment, transition portions lie between abrasive portion 160 and the distal and proximal shoulders. In the embodiment illustrated, a proximal transition portion 164 and a distal transition portion 162 lie between abrasive portion 160, and proximal shoulder 156 and distal shoulder 158, respectively. In one embodiment the transition portions have a straight taper while in another embodiment the transition portions have a rounded taper. In yet another embodiment, the transition portions are substantially larger, and can approach the size of the shoulders. In this embodiment, the larger transition portions impart a dumbbell appearance to the atherectomy burr.

Figure 11:
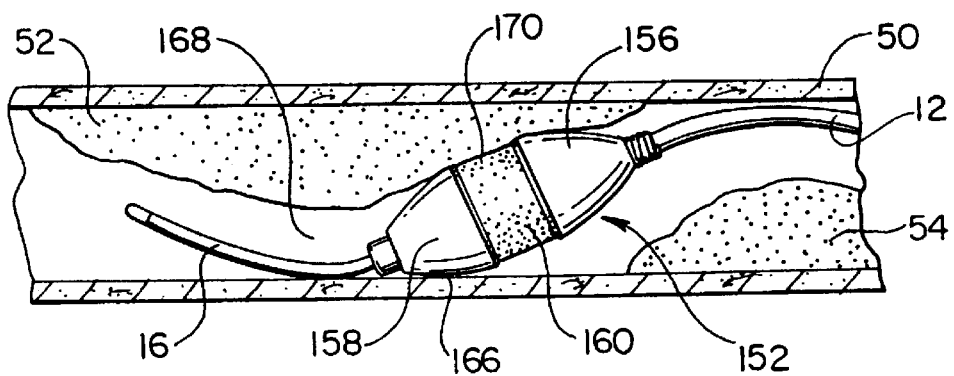
FIG. 11 is a fragmentary, side, perspective view of the atherectomy device disposed within a lumen having an asymmetrical lesion.

Referring now to FIG. 11, atherectomy device 150 is illustrated disposed within vessel 50 between a first deposit 52 and a second deposit 54. Deposits 52 and 54 are deposited on opposite sides of vessel 50, creating a tortuous path through the vessel. The path illustrated forces atherectomy burr 152 to cant relative to the vessel longitudinal axis, forcing distal shoulder 158 into contact with the wall of vessel 50 as indicated at 166. If distal shoulder region 166 was abrasive, the rotating, abrasive portion could be forced into contact with the vessel wall. If drive shaft 16 is pushed in a distal direction with sufficient force, it is also possible in some vessel geometries, to force proximal shoulder 156 into an opposite wall of the vessel as well.

As indicated at 170, abrasive portion 160 is brought to bear against deposit 52, allowing the unwanted material to be removed by the rotating atherectomy burr. At the same time, less abrasive distal shoulder 166 is presented to the wall of vessel 50. As burr 152 is advanced over guide wire 16, distal shoulder 166 will follow a path between the vessel wall and the deposit, and will present abrasive portion 160 to the deposit in region 168. At this location, distal shoulder 166 can act to align burr 152 with the path or channel between the deposit and the vessel wall. An inwardly projecting portion of deposit 52 will be presented to recessed, abrasive portion 160, while the smooth vessel wall will not substantially protrude into the recessed, abrasive portion. The deposit can be removed while the vessel wall remains untouched by the abrasive.

The cam action of the burr shoulders thus acts to align the abrasive or cutting action of the burr with the path through the vessel and deposits. The improved burr can reduce the wear on a vessel wall associated with cutting the corner of a bifurcated ostial lesion.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An ablation burr for removing deposits from a patient's vessel or stent, comprising:

a solid burr body having a distal and a proximal end and a leading concave surface, the leading concave surface extending from a generally smooth distal tip to a smooth shoulder that is proximal to the distal tip, wherein the concave surface has a radius about a central axis of the burr that lies beneath an imaginary line that extends between the distal tip and the smooth shoulder; and an abrasive on the concave surface that removes deposits from the patient's vessel or stent.

2. The ablation burr of claim 1, wherein the burr body includes a convex outer surface that extends from the end point of the leading concave surface to the proximal end of the burr.

3. An ablation burr for removing deposits from a patient's vessel or stent, comprising:

a burr body having a distal and a proximal end and a leading concave surface, the leading concave surface extending from a generally smooth distal tip to a smooth shoulder that is proximal to the distal tip, wherein the concave surface has a radius about a central axis of the burr that is entirely below an imaginary line that extends between the distal tip and the smooth shoulder; and an abrasive on the concave surface that removes deposits from the patient's vessel or stent.

* * * * *

UNITED STATES PATENT AND TRADEMARK OFFICE
CERTIFICATE OF CORRECTION

PATENT NO. : 6,156,048
DATED : December 5, 2000
INVENTOR(S) : E. Wulfman

It is certified that error appears in the above-identified patent and that said Letters Patent is hereby corrected as shown below:

Item [19],
Line 2, Caption, "Wulfman et al." should read -- Wulfman --

Item [75],
Lines 1-6, delete ";Lucas Gordon, Redmond; Robert Barry, Kirkland; Brandon Shuman, Seattle; David Dillard, Redmond; Verivada Chandrasekaran, Mercer Island, all of Wash." and insert therefor --, Wash. --

Item [56],
References Cited (Other Publications), after the section titled " FOREIGN PATENT DOCUMENTS", insert the following:
-- OTHER PUBLICATIONS
Supplementary European Search Report, European application number EP 98 90 8986 --

Signed and Sealed this

Thirteenth Day of November, 2001

Attest:

NICHOLAS P. GODICI
Attesting Officer    Acting Director of the United States Patent and Trademark Office